United States Patent [19]
Takino et al.

[11] Patent Number: 5,195,357
[45] Date of Patent: Mar. 23, 1993

[54] METHOD FOR MEASURING RESISTANCE TO SLIPPAGE

[75] Inventors: Hiroshi Takino; Makoto Komai; Noriyuki Isobe, all of Ibaraki, Japan

[73] Assignee: Toyo Tire & Rubber Company Limited, Osaka, Japan

[21] Appl. No.: 929,501

[22] Filed: Aug. 18, 1992

Related U.S. Application Data

[63] Continuation of Ser. No. 584,121, Sep. 18, 1990, abandoned.

[30] Foreign Application Priority Data

Sep. 18, 1989 [JP] Japan .................................. 1-243239

[51] Int. Cl.⁵ ............................................. G01N 19/02
[52] U.S. Cl. ........................................... 73/9; 73/146; 374/45
[58] Field of Search ........................... 73/9, 10, 8, 146; 374/45

[56] References Cited

U.S. PATENT DOCUMENTS

| 2,296,657 | 9/1942 | Wallace | 73/9 |
| 2,883,855 | 4/1959 | Spengler et al. | 73/10 |
| 3,518,872 | 7/1970 | Tiner et al. | 73/9 |
| 3,852,993 | 12/1974 | Bronovets et al. | 73/9 X |
| 4,909,073 | 3/1990 | Takahashi et al. | 73/9 X |

FOREIGN PATENT DOCUMENTS 2310139  9/1974  Fed. Rep. of Germany ............ 73/9

Primary Examiner—Thomas P. Noland

[57] ABSTRACT

Method for measuring resistance to slippage comprising the steps of mounting a sample of rubber at the bottom of a pendulum freely swinging on a shaft, sliding the sample of rubber along a road surface sample which is either dry or wet during swinging of the pendulum, measuring kinetic energy loss of the pendulum due to sliding of the sample thus obtaining resistance to slippage, in combination with the step of either heating or cooling the sample of rubber to a predetermined temperature for performing the method.

18 Claims, 3 Drawing Sheets

METHOD FOR MEASURING RESISTANCE TO SLIPPAGE

This application is a continuation of application Ser. No. 07/584,121 filed on Sept. 18, 1990, now abandoned.

BACKGROUND OF THE INVENTION

1. Field of the Invention the present invention relates to a method for accurately measuring resistance to a slippage of rubber employed as tread rubber for use in an automobile tire.

2. Disclosure of the Prior Art

It is heretofore been well known to use a pendulum type apparatus for measuring resistance to slippage as a simple method for measuring coefficient of friction with a dry road surface or a wet road surface. This conventional method for measuring resistance to slippage comprises the steps of mounting a sample of rubber at the bottom of a pendulum, dropping the pendulum freely from a horizontal position and oscillating it, sliding the sample of rubber with respect to a plate similar to a road surface at a lower end position of the pendulum with a certain pressure, measuring the extent of upward movement of the pendulum thereby obtaining energy loss due to sliding friction between the sample of rubber and the road surface-like plate. Thus, rubber's resistance to slippage can be very simply measured.

It is certain that measurement of resistance to slippage can be simply performed with the mentioned conventional pendulum type apparatus of simple construction. But when comparing a value obtained by means of the apparatus with a result of measurement of resistance to slippage of a tire obtained by actually driving it on wet road and dry road, the tire being made of a tread rubber composed of the same rubber as the mentioned sample rubber, it is recognized that there is a relatively reasonable positive corelation therebetween in the aspect of wet road surface test, but that there is substantially no such correlation in the aspect of dry road surface test. As a result, a problem exists in that the mentioned conventional method for measuring resistance to slippage using the measuring apparatus with a pendulum is useful only for the evaluation of resistance to slippage on wet road surface, and is not useful for evaluation of resistance to slippage on dry road surface.

SUMMARY OF THE INVENTION

Accordingly, it is an object of the present invention to provide a method for measuring resistance to slippage in which resistance to slippage of tread rubber on both wet and dry road surfaces can be exactly evaluated by a simple pendulum type apparatus for measuring resistance to slippage.

In order to accomplish the foregoing object, as a result of aggressive and repeated research, it has been found that a value measured by means of the conventional pendulum type apparatus is not consistent with a resistance value of a tire obtained by actual driving in the aspect of dry road surface condition, because there is a difference between the temperature of the tread rubber of tire under actual driving conditions and that of a sample of rubber at the time of measurement by means of the pendulum type measuring apparatus considering that resistance to splippage on dry road surface varies largely depending upon the temperature of the sample of rubber. Accordingly, for measuring resistance to slippage by means of pendulum type measuring apparatus, it is essential to adjust temperature of the sample of rubber to a temperature of a tire under driving conditions.

More specifically, the method for measuring resistance to slippage in accordance with the invention compries the steps of mounting a sample of rubber at the bottom of a pendulum freely swinging on a shaft, sliding the sample of rubber along a road surface sample which is either dry or wet during oscillation of the pendulum, measuring kinetic energy loss of the pendulum due to sliding of the sample thus obtaining resistance to slippage, in combination with the step of either heating or cooling the sample of rubber to a predetermined temperature for performing the method.

Other objects and advantages of the invention will become apparent in the course of the following description with reference to the accompanying drawings. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

In the drawings forming a part of the present application but which are given by way of illustration only, and thus are not limitative of the present invention, and wherein like reference numerals designate like parts.

DESCRIPTION OF THE PREFERRED EMBODIMENTS

Figure 1:
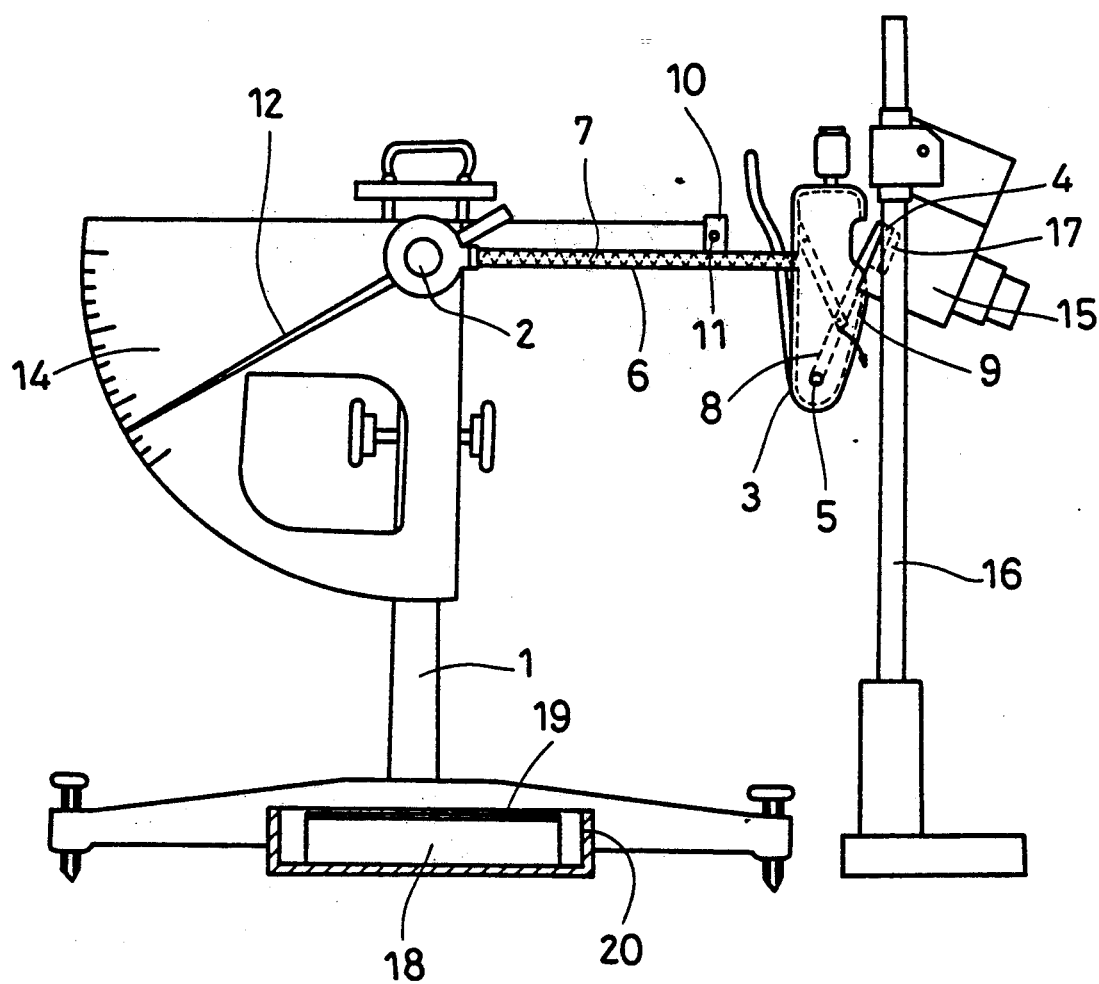
FIG. 1 is a front view of an example of the measuring apparatus used in the method for measuring resistance to slippage in accordance with the present invention.

Referring now to FIG. 1, reference numeral (1) denotes a post which is vertically telescopic by manually operating a height adjustment knob (13). A shaft (2) is fixed on the post (1), and a pendulum (3) is turnably mounted around the shaft (2). A sample mount (4) is attached at the bottom of the pendulum (3) is such a manner as to be oscillatable on a shaft (5). An impetus is given to the sample mount (4) so as to turn in the direction of the arrow by a compressive coil spring (7) disposed in a cylindrical arm (6) of the pendulum (3) through a link mechanism (8). Accordingly, the sample mount (4) is normally held in contact with a lower edge (9) of the pendulum (3).

Numeral (10) denotes a stopper for engagedly holding the mentioned arm (6) of the pendulum (3) in a horizontal state. The stopper (10) is disengaged by depressing a release button (11) so that the pendulum (3) may oscillate freely. Numeral (12) denotes a drag pointer which is fitted on the shaft (2) in such a manner as to be turnable by a very small frictional force. The drag pointer (12) turns clockwise on the scale plate (14)

together with the pendulum (3) to point to the highest position reached by the pendulum (3) on the left side.

Numeral (15) denotes a temperature adjustment device adjustably mounted on a post (16), and in which a sample of rubber (17) mounted on the sample mount (4) is accommodated so as to be heated or cooled to a predetermined temperature.

Numeral (18) denotes a road surface sample mount made of a metal block on which a road surface sample (19) is pasted and horizontally placed on a road surface sample tank (20) in a dry or wet state, whereby the sample of rubber (17) may slide on the road surface sample at the lower end of oscillation of the pendulum (3). The temperature adjustment device (15) is provided on either the road surface sample mount (18) or the road surface sample tank (20) to adjust temperature of the road surface sample (19).

For performing measurement of resistance to slippage of rubber with the use of the pendulum type measuring apparatus shown in FIG. 1, first the sample of rubber (17) is mounted on the sample mount fit at the bottom of the pendulum (3), while placing the road surface sample mount (18) with the road surface sample (19) in front of the post (1). The height adjustment knob (13) for adjusting height of the post (1) is then adjusted in such a manner that the sample of rubber (17) slides on the road surface sample (19) exactly over a certain length when oscillating the pendulum (3). Then the pendulum (3) is retained by the stopper (10) at the position where the arm (6) is horizontal. At this time, the temperature adjustment device (15) is engaged with the sample of rubber (17) to heat or cool the sample to a predetermined temperature.

The road surface sample (19) is also adjusted to a predetermined temperature by adjusting temperature of either the road surface sample amount (18) or the road surface sample tank (20). Wet road surface condition is accomplished by applying water to the road surface sample tank (20).

Figures 2A, 2B:
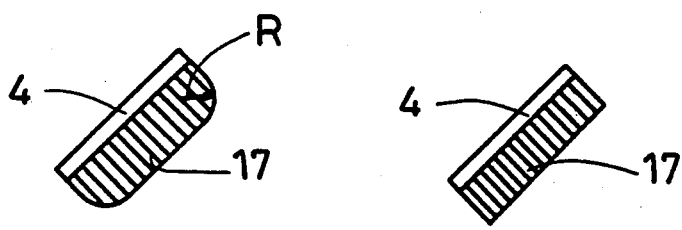
FIGS. 2 a and b are sectional views each showing a sample of rubber.

It is preferable that the sample of rubber (17) mounted on the sample mount (4) is so shaped as to have a certain curvature radius R at the corners as shown in FIG. 2a illustrating a sectional view of the sliding portion of the sample of rubber (17) cut in parallel to the oscillating side of the pendulum (3), i.e., cut in parallel to the sliding direction. The curvature radius R is preferably in the range of 3 to 30 mm and, more preferably, in the range of 4 to 10 mm. In the method for measuring resistance to slippage by means of the conventional pendulum type measuring apparatus, resistance to slippage is measured on a sample of rubber (17) having rectangular corners as shown in FIG. 2b. When measuring a sample of rubber (17) of such a shape, measured values vary widely and accurate measurement is difficult.

After the sample of rubber (17) and the road surface sample (19) reaching a predetermined temperature, the temperature adjustment device (15) is released from the sample of rubber (17) and, at the same time, the release button (11) of the stopper (10) is depressed to release the retention, thereby dropping the pendulum (3) and sliding the sample of rubber (17) on the road surface sample (19). The pendulum (3), after the sliding movement between the sample of rubber (17) and the road surface sample (19), further turns together with the drag pointer (12) to cause the same to reach and remain in the highest point.

Contact pressure between the sample of rubber (17) and the road surface sample (19) is at the time of sliding substantially kept constant by the force urged to turn the sample mount (4) in the direction of the arrow by means of the compressive coil spring (7).

If there is no sliding movement between the sample of rubber (17) and the road surface sample (19), the pendulum (3) turns to its horizontal position on the left side and a part of kinetic energy is losed as friction loss due to the slide, thus the friction loss being quantitatively represented by the drag pointer (12).

It is generally understood that an energy loss due to friction between tread rubber of a tire and road surface is caused by pure friction energy, hysteresis loss and shearing force which tears off the rubber overcoming cohesive force of the rubber. However, when suffering a certain deformation, hysteresis loss varies a lot depending upon temperature of the rubber. Energy loss due to shearing force may be relatively small in general. However, depending upon configuration of the sample of rubber, particularly in the event of dry road surface which may break a sharp corner portion of the sample of rubber, the energy loss due to shearing force may be considerable. For that reason, it is preferable that the sliding portion of the sample of rubber (17) has no such sharp corner.

In the method for measuring resistance to slippage in accordance with the present invention, since measurement is carried out under substantially the same temperature condition as that of actual driving of the tire on a road surface, a quite reasonable consistency is found between the measured value obtained by measuring a sample of rubber and the friction coefficient of the tire made of the same rubber as the sample one employed as tread rubber, whether it is a dry road surface or wet road surface.

Accordingly, when a new rubber composition is employed as tread rubber of a tire, friction coefficient of the tire can be exactly anticipated by measuring resistance to slippage thereof by the measuring method of the invention. Such anticipation is very useful for selection of tread rubber as a matter of course.

EXAMPLE

Using the apparatus for measuring resistance to slippage illustrated in FIG. 1, resistances to slippage were measured on samples of rubber of various rubber compositions changing temperatures of the samples of rubber (17). Each rubber sample (17) was prepared to be 60 mm in width (direction making a right angle to the sliding direction) ×30 mm in length ×6 mm in thickness and 5 mm in curvature radius of corner portions. A new road surface sample (19) was prepared by pasting up a friction sheet composed of abrasive grain and synthetic resin onto the road surface sample mount (18) for each measurement. Sliding distance between the sample of rubber (17) and the road surface sample (19) was accurately adjusted to 150 mm by adjusting the height adjustment knob.

Resistances to slippage of a sample of rubber (17) were measured by the method in accordance with the invention on both dry and wet road surface conditions, then were represented by indexes of resistance to slippage, i.e., skid number. Further, a tire whose tread rubber was made of the same rubber as the sample rubber (17) was mounted on a trailer by the method set forth in the consumer's information rules in the United States, i.e., in the paragraph (F) of the United Tire Quality Grading Standards, for both dry and wet road surface conditions. The trailer was then driven at the speed of 64.4 km/h and, during the driving, one of the trailer's tires was locked for measuring a force acting on and between the locked tire and the road surface. As a result of such measurement, dry road surface friction coefficient Dry $\mu a$ and wet road surface friction coefficient Wet $\mu a$ were obtained.

For representation by skid number, first the resistance to slippage was obtained by measuring a standard rubber which as the same one as the tread rubber used in the standard tire subject to the measurement of the mentioned dry and wet road surface coefficients. This measurement was carried out on the sample of rubber at 25° C. on the dry road surface employing the measuring method in accordance with the invention. The resistance to slippage (friction energy loss) thus obtained was established as a reference value 100, on the basis of which every resistance to slippage of the sample of rubber (17) obtained for each condition was represented by index. In other words, the skid numbers were obtained by the following expression:

Skid number = (sample rubber's resistance to slippage/standard rubber's resistance to slippage on dry road surface at 25° C.) × 100.

Figure 3:
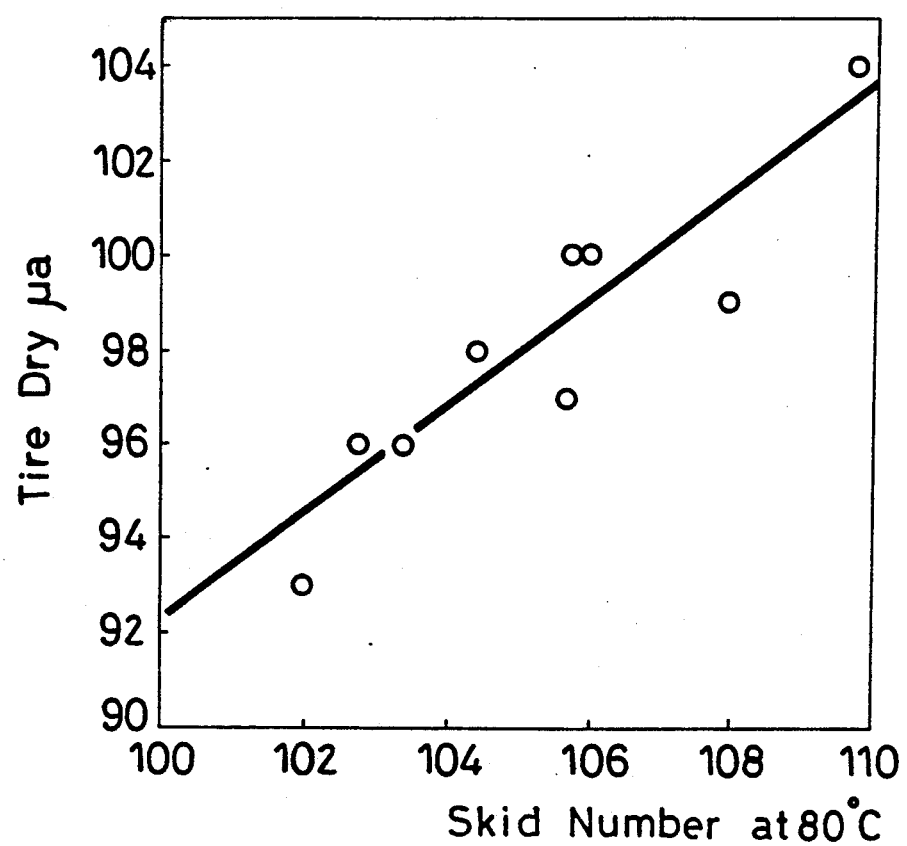
FIGS. 3 and 4 are graphs each showing a relation between skid number obtained by means of the pendulum type measuring apparatus of the invention and actual friction coefficient of a tire.
Figure 4:
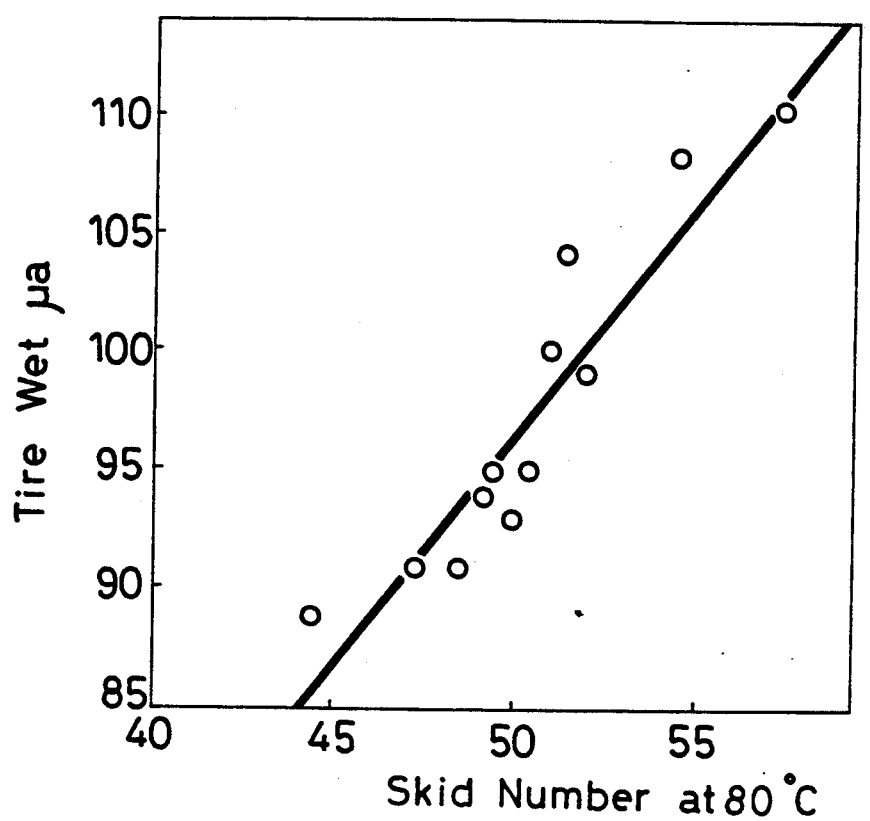

FIG. 3 shows a relation between the skid number on the dry road surface obtained by the measuring method in accordance the invention and the metioned dry road surface friction coefficient Dry $\mu a$, and FIG. 4 shows a relation between the skid number on the wet road surface and the wet road surface friction coefficient wet $\mu a$. It is understood from these drawings that there is a very significant correlation between the measured values obtained by respective methods in both dry and wet road surfaces.

Figure 5:
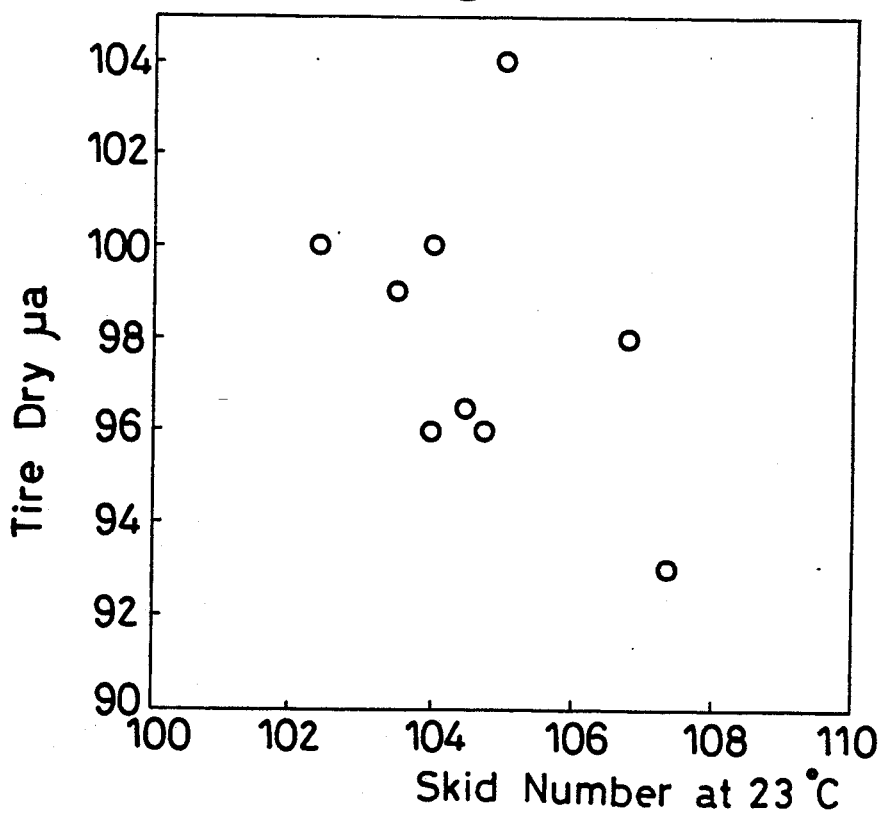
FIG. 5 is a graph showing a relation between skid number obtained by means of the conventional pendulum type measuring apparatus and actual friction coefficient of tire.

As a comparative example, FIG. 5 shows a relation between skid number obtained by means of the conventional measuring method on sample of rubber on dry road surface at the room temperature of 23° C. without adjusting the temperature of the sample of rubber and the mentioned dry road surface friction coefficient Dry $\mu a$. It is understood from this drawing that substantially no correlation is found between the measured values.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for measuring resistance to slippage comprising the steps of:
   using a sample of rubber having a sectional form of a sliding portion cut generally parallel to a sliding direction, the sample being shaped in a generally circular arch;
   mounting the sample of rubber at a bottom of a pendulum, the pendulum being freely swingable on a shaft;
   sliding the sample of rubber on a road surface sample during swinging of the pendulum, the road surface sample being one of dry and wet;
   coordinating temperatures of the sample of rubber and the road surface sample by one of heating and cooling the samples;
   measuring kinetic energy loss of the pendulum due to sliding of the sample of rubber and thereby obtaining resistance to slippage.

2. The method according to claim 1, wherein during the step of coordinating, temperature of the sample of rubber is adjusted to a temperature of a rubber tread of a tire during driving of the tire.

3. The method according to claim 1, wherein the step of coordinating further comprises the step of adjusting the temperature of the road surface sample to a predetermined temperature.

4. The method according to claim 1, wherein the step of using further comprising using as the sample of rubber a sample with an arch having a radius of curvature being within a range of 4 to 10 mm.

5. The method according to claim 1, wherein during the step of sliding, the road surface sample is dry.

6. The method according to claim 1, wherein during the step of sliding, the road surface sample is wet.

7. The method according to claim 1, wherein the step of coordinating comprises heating the sample of rubber.

8. The method according to claim 1, wherein the step of coordinating comprises cooling the sample of rubber.

9. The method according to claim 1, wherein during the step of coordinating, temperature of the road surface sample is adjusted to a temperature of an actual road surface.

10. A method for measuring resistance to slippage comprising the steps of:
    mounting a sample of rubber at a bottom of a pendulum, the pendulum being freely swingable on a shaft with the sample of rubber;
    sliding the sample of rubber at the bottom of the pendulum on a road surface during swinging of the pendulum, the road surface sample being one of dry and wet;
    changing temperature of the sample of rubber at the end of the pendulum by one of heating and cooling with means therefore adjacent the end of the pendulum during the temperature change, the step of changing temperature of the sample of rubber occurring before the step of sliding; and
    measuring kinetic energy loss of the pendulum due to sliding of the sample of rubber and thereby obtaining resistance to slippage.

11. The method according to claim 10, further comprising the step of changing temperature of the road surface sample by one of heating and cooling, the step of changing the temperature of the road surface sample occurring before the step of sliding.

12. The method according to claim 10, wherein during the step of changing, the temperature of the sample of rubber is adjusted to a temperature of a rubber tread of a tire during driving of the tire.

13. The method according to claim 10, further comprising the step of using as the sample of rubber a sample having a sectional form of a sliding portion cut generally parallel to a sliding direction, the sample being shaped in a generally circular arch with a radius of curvature being within a range of 4 to 10 mm.

14. The method according to clam 10, wherein during the step of sliding, the road surface sample is dry.

15. The method according to claim 10, wherein during the step of sliding, the road surface sample is wet.

16. The method according to claim 10, wherein the step of changing comprises heating the sample of rubber.

17. The method according to claim 10, wherein the step of changing comprises cooling the sample of rubber.

18. The method according to claim 10, wherein during the step of changing, the temperature of the road surface sample is adjusted to a temperature of an actual road surface.

* * * * *